United States Patent [19]

Hammer

[11] Patent Number: 5,133,454
[45] Date of Patent: Jul. 28, 1992

[54] INTRAVENOUS CATHETER BIOHAZARD PREVENTION PACKAGING DEVICE

[76] Inventor: Steven G. Hammer, 831 S. Miller, Chicago, Ill. 60607

[21] Appl. No.: 624,700

[22] Filed: Dec. 6, 1990

[51] Int. Cl.$^5$ ............................................. D65D 83/10
[52] U.S. Cl. ................................ 206/364; 206/366; 206/470
[58] Field of Search ................ 206/364, 365, 366, 470

[56] References Cited

U.S. PATENT DOCUMENTS

| | | | |
|---|---|---|---|
| 685,091 | 10/1901 | Becton | 206/365 |
| 3,625,353 | 12/1971 | Ishii | 206/365 |
| 3,709,223 | 1/1973 | Macalalad et al. | 206/364 X |
| 4,005,776 | 2/1977 | Seeley | 206/364 X |
| 4,015,709 | 4/1977 | Millet | 206/366 |
| 4,106,621 | 8/1978 | Sorensen | 206/470 X |
| 4,184,593 | 1/1980 | Dorr | 206/365 |
| 4,438,845 | 3/1984 | Mochow | 206/366 |
| 4,569,442 | 2/1986 | Bushey | 206/470 X |
| 4,643,722 | 2/1987 | Smith, Jr. | 604/192 |
| 4,753,345 | 6/1988 | Goodsir et al. | 206/365 X |
| 4,917,243 | 4/1990 | Abrams et al. | 206/365 |
| 4,921,096 | 5/1990 | McFarlane | 206/349 |
| 4,927,018 | 5/1990 | Yang et al. | 206/305 |
| 4,938,354 | 7/1990 | Hernandez | 206/365 |
| 4,938,462 | 7/1990 | Gould | 206/470 |

FOREIGN PATENT DOCUMENTS

| | | |
|---|---|---|
| 485740 | 2/1918 | France . |
| 1408369 | 7/1965 | France ................ 206/364 |
| 1474882 | 2/1967 | France . |
| 715350 | 9/1954 | United Kingdom . |
| 1125568 | 8/1968 | United Kingdom . |

OTHER PUBLICATIONS

Protectiv I.V. Catheter Safety System Critikon a Johnson-Johnson Company Brochure.

Primary Examiner—Paul T. Sewell
Assistant Examiner—BethAnne Cicconi
Attorney, Agent, or Firm—Hill, Van Santen, Steadman & Simpson

[57] ABSTRACT

This invention relates to a packaging system for a needle and catheter which can be unsealed and the lid opened so that the catheter and needle can be removed after which the needle and catheter are inserted in a patient and then the needle is removed and replaced in the container and the container is closed so that the needle cannot accidentally contaminate and injure personnel.

6 Claims, 1 Drawing Sheet

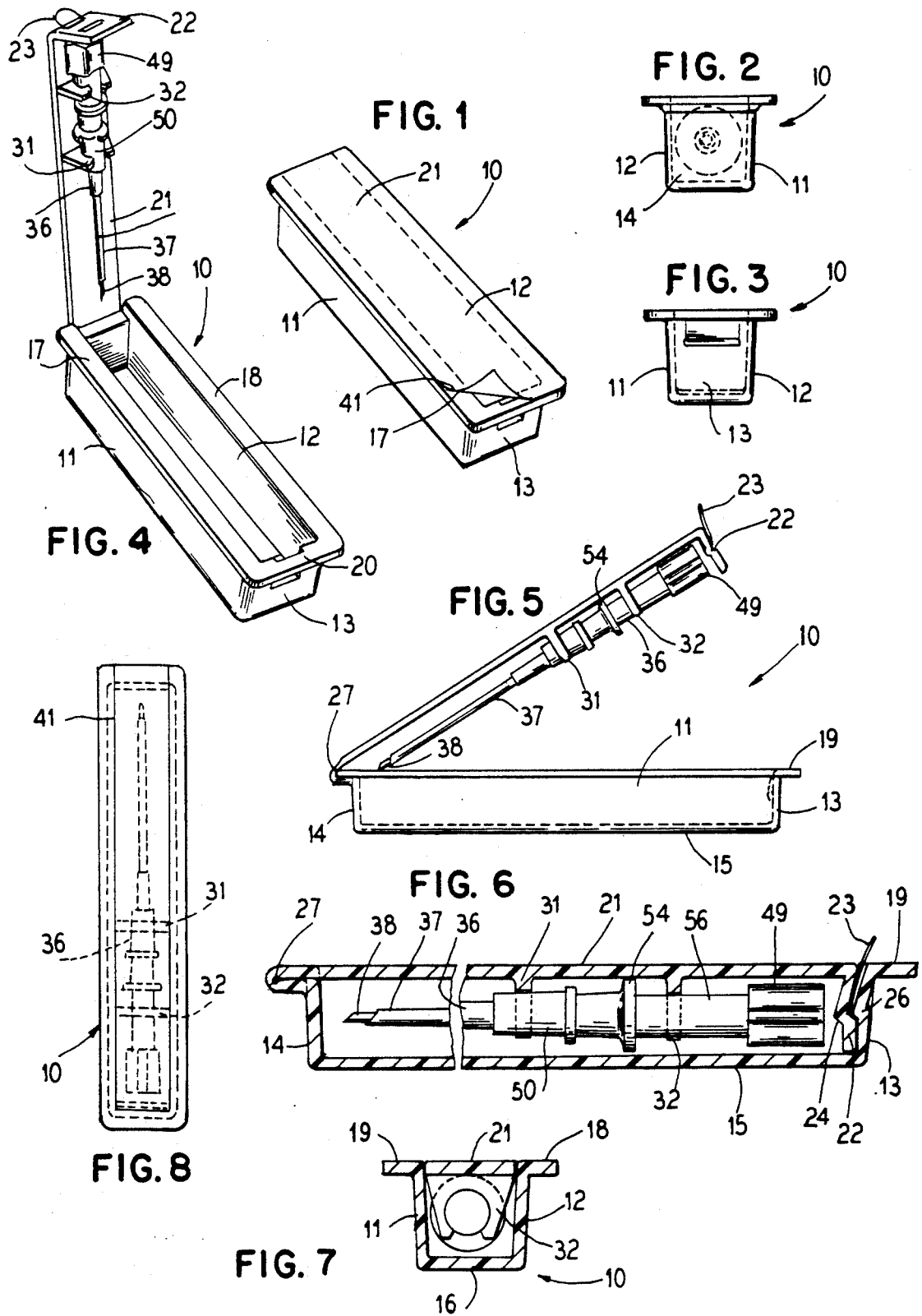

INTRAVENOUS CATHETER BIOHAZARD PREVENTION PACKAGING DEVICE

BACKGROUND OF THE INVENTION

1. Field of the Invention

This invention relates in general to a new intravenous catheter package for use in health care applications and, in particular, to a package for a needle of a catheter so as to prevent the needle from accidently injuring a user.

2. Description of Related Art

Currently, catheters range in length form ¾" to 2½" which are packaged in sterile plastic and paper containers measuring 1–5½". After the IV catheter has been removed from the package and inserted into a vein, the needle is removed and should be disposed of since it may be contaminated. However, since the IV catheter must be connected to an IV tubing immediately after insertion, the needle is frequently placed on the floor or mattress which poses a dangerous situation.

The Critikon Company has a plastic cover for sliding over the needle as it is removed, but such device is relatively complicated and expensive. See also U.S. Pat. Nos. 4,938,354, 4,927,018, 4,921,096, 4,643,722, 4,917,243, French Patent 485,740, British Patent 715,350 and French Patent 1,474,882.

SUMMARY OF THE INVENTION

The present invention comprises a catheter packaging structure wherein the package will provide a convenient and safe disposable receptacle for the needle and which can then be closed so as to prevent the needle from being a hazard. The open box receives the used needle at the bedside and then can be snapped shut for a safe disposal package and the packaging material is heavy enough so that the needle cannot readily puncture the package and thus provides a safe disposal unit for the needle.

The present invention provides a sterile needle and catheter in a container which is sealed and which can be opened and the needle and catheter removed and inserted into a patient after which the needle is removed and placed into the container and the container is closed so as to provide a protective package for the needle to prevent accidents with the used needle.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

BRIEF DESCRIPTION OF THE DRAWINGS

FIG. 1 is a protective view of the invention;

FIG. 2 is a first end view of the invention;

FIG. 3 is a second end view of the invention;

FIG. 4 is a prospective view showing the protective seal and lid of the invention in the open position;

FIG. 5 is a side plan view showing the lid in the open position;

FIG. 6 is a partially cut-away view showing the invention;

FIG. 7 is a sectional view showing the invention; and

FIG. 8 is a top plan view of the invention.

DESCRIPTION OF THE PREFERRED EMBODIMENTS

The invention comprises a container 10 which has sidewalls 11 and 12 and end walls 13 and 14 and a bottom wall 15 and a cover 21 which is attached by a hinge 27. Around the top edge of the container is formed a rim 17, 20 and 18 as shown, for example, in FIG. 4 and the lid 21 is formed with a forward downwardly extending portion 22 which fits into the forward portion 13 of the container as shown in FIG. 6. A detent 24 is shown on the portion 22 and mates with a detent 26 formed on the front wall 13 of the container. A handle 23 is attached to the lid 21 adjacent portion 22 so that the lid can be removed from the container.

A layer of sealing paper 41 is mounted over the lid 21 so as to seal the container to form a sterile package during storage and before the packaging is open to remove the needle and catheter 36.

On the inside of the lid 21 are formed a pair of C-shape brackets 31 and 32 as shown in FIGS. 4, 5 and 6 into which a needle 38 and catheter 36 are received. The catheter 36 has a tubular portion 37 which surrounds the needle 38 and is attached to an upper end portion 50 as shown in FIG. 4. The needle 38 has a handle portion 54 and a tubular portion 56 which connects to the end 49.

In use, the paper seal 41 is removed from the container 10 and the lid 21 is opened using the handle 23. The catheter and needle 36 and 38 assembly is removed from the clamps 31 and 32 and the needle 38 and catheter 36 are inserted into a patient. After insertion, the needle 38 is removed by the handle 54 or end 49 from the catheter 37 so that the catheter 37 remains in the patient and then the needle 38 is placed into the container 10 and the lid 21 is closed so that the needle 38 is protected by the container 10 and cannot accidentally contaminate anyone.

It is to be realized that the needle 38 must be removed and a tube attached to the catheter end portion 50 very rapidly so that the needle must be disposed of in a rapid fashion so as to prevent excessive blood from passing through the catheter 36 before the tube is attached. Thus, the present invention allows the needle to be quickly inserted into the container and the lid 21 then closed so that a tube not shown can be rapidly attached to the catheter. Since the needle 38 has been placed into the container 10 and the lid 21 has been closed, the needle no longer presents a health hazard.

Although the invention has been described with respect to preferred embodiments, it is not to be so limited as changes and modifications can be made which are within the full intended scope of the invention as defined by the appended claims.

We claim as our invention:

1. A container and protective device including a needle and catheter comprising, a catheter formed of a tubular portion and having a tube receiving portion at one end, a needle receivable through said tube receiving and tubular portions of said catheter and formed with a handle portion, a container with sidewalls, and end walls which extend upwardly and terminate in flanges substantially perpendicular to said sidewalls and end walls, and a bottom with a lid which is hinged to said container at one of said flanged end walls and meets an interior perimeter of the flanges in a closed position thereby forming a planar surface extending the length of the container, the lid having a clamp formed with an opening, said needle and catheter stored in said clamp on said lid, such that said needle and catheter can be removed from said clamp when said lid is open, and so that said needle can be removed from said catheter and placed in said container after use and the lid can be closed to prevent said needle from causing injury, because the lid and said container having a detent formed between them for preventing inadvertent opening of the container and lid.

2. A container and protective device according to claim 1 including a paper seal mounted over said lid on said container.

3. A container and protective device according to claim 1 wherein said lid has one end pivoted to said container.

4. A container and protective device including a needle and catheter comprising, a catheter formed of a tubular portion and having a tube receiving portion at one end, a needle receivable through said tube receiving and tubular portions of said catheter and formed with a handle portion, a container with sidewalls, end walls which extend upwardly and terminate in flanges substantially perpendicular to said sidewalls and end walls and a bottom and with a lid formed with an opening said lid being hinged to said container at one of said flanged end walls and meets an interior perimeter of the opening in a closed position thereby forming a planar surface extending the length of the container, the lid having said needle and catheter stored in said container, such that said needle and catheter can be removed from said container when said lid is open, and so that said needle can be removed from said catheter and placed in said container after use and the lid can be closed to prevent said needle from causing injury because the lid and container have a detent formed between them for preventing inadvertent opening of the container and lid.

5. A container and protective device according to claim 4 including a paper seal mounted over said lid on said container.

6. A container and protective device according to claim 4 wherein said lid has one end pivoted to said container.

* * * * *